United States Patent
Mutti et al.

(10) Patent No.: US 8,127,767 B2
(45) Date of Patent: Mar. 6, 2012

(54) DEVICE FOR DELIVERING RESPIRATORY GAS DIRECTLY INTO THE NOSE OF A USER

(75) Inventors: Franco Mutti, Sonceboz-Sombeval (CH); Jurg Gfeller, Villeret (CH)

(73) Assignee: Innosuisse Management AG, Murten (CH)

( * ) Notice: Subject to any disclaimer, the term of this patent is extended or adjusted under 35 U.S.C. 154(b) by 821 days.

(21) Appl. No.: 12/225,073

(22) PCT Filed: Mar. 16, 2007

(86) PCT No.: PCT/EP2007/052535
§ 371 (c)(1),
(2), (4) Date: Sep. 12, 2008

(87) PCT Pub. No.: WO2007/107526
PCT Pub. Date: Sep. 27, 2007

(65) Prior Publication Data
US 2009/0101154 A1   Apr. 23, 2009

(30) Foreign Application Priority Data
Mar. 17, 2006   (EP) .................................. 06111351

(51) Int. Cl.
*A61M 15/08*   (2006.01)
*A62B 7/00*   (2006.01)
(52) U.S. Cl. .............................. 128/207.18; 128/204.18
(58) Field of Classification Search ............ 128/204.18, 128/204.21, 205.24, 206.21, 206.24, 207.18
See application file for complete search history.

(56) References Cited

U.S. PATENT DOCUMENTS

| 4,660,555 | A | * | 4/1987 | Payton | 128/207.18 |
| 4,936,298 | A | * | 6/1990 | Nishina et al. | 128/205.13 |
| 5,291,897 | A | | 3/1994 | Gastrin et al. | |
| 5,533,506 | A | * | 7/1996 | Wood | 128/207.18 |
| 5,535,739 | A | | 7/1996 | Rapoport et al. | |
| 5,724,965 | A | * | 3/1998 | Handke et al. | 128/207.13 |
| 6,012,455 | A | * | 1/2000 | Goldstein | 128/207.18 |
| 6,561,188 | B1 | | 5/2003 | Ellis | |
| 6,776,163 | B2 | * | 8/2004 | Dougill et al. | 128/207.18 |
| 6,857,428 | B2 | * | 2/2005 | Thornton | 128/206.21 |
| 2003/0168067 | A1 | * | 9/2003 | Dougill et al. | 128/207.18 |
| 2005/0166927 | A1 | * | 8/2005 | McAuley et al. | 128/207.18 |

FOREIGN PATENT DOCUMENTS

| EP | 1 314 445 A1 | 5/2003 |
| EP | 1 459 779 A1 | 9/2004 |
| FR | 2 827 778 A1 | 1/2003 |
| WO | WO 99/58181 A1 | 11/1999 |
| WO | WO 03/068301 A1 | 8/2003 |

* cited by examiner

*Primary Examiner* — Justine Yu
*Assistant Examiner* — Rachel Young
(74) *Attorney, Agent, or Firm* — Oliff & Berridge, PLC

(57) ABSTRACT

A device for delivering respiratory gas directly into the nose of a user, for example for use in the treatment of sleeping disorders, in particular sleep apnea. This device for delivering respiratory gas directly into the nose of a user includes a hollow elastic membrane insertable into a nostril of the user and a part, inserted in the cavity of the elastic membrane, which part has a passage extending from one end to an opposite end of the inserted part, and it is characterized in that the inserted part further includes breathing channels which are located in the wall of the inserted part and extend from one end to an opposite end of the inserted part. The invention also relates to a method for producing the device according to the invention, a set and a system for delivering respiratory gas directly into the nose of a user, and a method for assembling the system according to the invention.

20 Claims, 5 Drawing Sheets

DEVICE FOR DELIVERING RESPIRATORY GAS DIRECTLY INTO THE NOSE OF A USER

FIELD OF THE INVENTION

The invention relates to the delivery of respiratory gas directly into the nose of a user, for example for use in the treatment of sleeping disorders, in particular sleep apnea.

BACKGROUND TO THE INVENTION

In the treatment of sleeping disorders, such as sleep apnea (i.e. cessation of breathing while asleep), facial masks or nasal masks are normally used, as is known from the European patent EP 1 314 445, for example.

Such a mask covers the entire nose and a portion of the face. It is generally held over the whole head by a fastener made up of ties. The ties pull the mask toward the face with sufficient force so that a gas-tight seal is achieved between the mask and the face of the wearer.

In treatment of a sleep apnea syndrome, the patient must wear such a mask every night and for a very long time, usually lifelong. A positive pressure respiration is carried out with the mask. This therapy is known by the technical term CPAP therapy. CPAP stands for "Continuous Positive Airway Pressure", i.e. continuous positive pressure in the air passages. A CPAP conducts a continuous stream of air from a ventilator into the mask which the patient has to wear the whole night. An elevated pressure, which prevents a collapse of the airways, is thereby created in the nasal-pharyngeal cavity. The patient can breathe normally, and the typical syndromes no longer occur.

An important disadvantage of the use of this mask is that the mask must be put on with a relatively great amount of force against the face. Pressure points in the face, face wounds and suppuration often thereby occur. If the ties are not pulled sufficiently, however, eye irritation can occur.

Moreover at least 15 to 20 minutes a day must be spent in hygienic care and cleaning of the mask and CPAP device.

Furthermore the mask system is a disposable article. Nowadays a patient needs 2 to 4 mask systems a year, which results in a great financial and material expenditure.

Thus the suffering of a sleep apnea patient must be very great in order for him to accept today's state of the art in CPAP therapy and put up with the discomfort, limitations and handicaps from regular use of the mask over a long period of time.

Described in U.S. Pat. No. 5,291,897 is a fastening member for insertion in the nasal cavity or in the ear of a patient. This fastening member was developed for monitoring of the breathing of a patient during anesthesia and for taking breathing samples. When used against sleep apnea, this fastening member, and in particular the one shown in FIG. 5 of this patent, leads to a tingling in the nose of the patient or to nose irritation, even after removal of the fastening member.

The invention thus aims to prevent or lessen the above drawbacks and difficulties, and has the object to create an aid which is practical, light, comfortable, simple to manufacture and to use, and is inexpensive, and which follows along with (accompanies without any interference) all head and body movements of the wearer during sleep.

DISCLOSURE OF INVENTION

After long research, the inventors discovered that the tingling or the irritation in the nose of the user of a fastening member as described in the above-mentioned U.S. Pat. No. 5,291,897 can be prevented in that the expired air is better evacuated out of the nostril of the user.

After further research it was then discovered that a better removal of the expired air may be achieved in that this expired air in the nostril is removed through a distributed way.

Object of the invention is thus a device which enables a distribution of the expired air during its removal.

This object is achieved with a device according to the invention which comprises
 a hollow elastic membrane insertable in a nostril of the user, and
 a part inserted in the cavity of the elastic membrane, which part has a passage extending from one end to an opposite end of the inserted part,
 and which is characterized in that the inserted part further comprises breathing channels which are located in the walling of the inserted part and extend from one end to an opposite end of the inserted part.

Surprisingly, the inventors discovered another advantage of the device according to the invention: with use of the breathing channels for supply of inspired air, besides achieving a better distribution of this inspired air in the nostril, a better distribution in the nostril of a gaseous medicament, present in the inspired air, if necessary, is achieved.

According to an embodiment of the invention, the membrane has at least one rounded-off end.

According to another embodiment of the invention, the inserted part has at least one rounded-off or beveled end.

According to a further embodiment, the inserted part has at least one transverse hole, which, in the walling of the inserted part, extends between the passage and the outer surface of the inserted part.

Subject matter of the invention is also a method for producing a device according to the invention in which a part, having a passage and breathing channels which extend from one end to an opposite end of the inserted part, is inserted into the cavity of a hollow elastic membrane insertable in a nostril of the user, and the membrane is fixed to this part.

Another subject matter of the invention is a set for delivery of respiratory gas directly into the nose of a user, comprising:
 a device according to the invention, and
 a retaining device for firmly holding the device according to the invention in a nostril of the user.

According to an embodiment of the invention, the retaining device is attachable to a supply tube, which can dispense the respiratory gas.

According to another embodiment, the retaining device has a connecting part and a contact part.

The connecting part preferably has a bore at one end for the supply tube, and the contact part is located at an opposite end of the connecting part.

The contact part preferably has substantially the form of a plate that is turned toward the axis of the bore. This plate can be curved, if necessary.

A further preferred embodiment of the invention consists in that the surface of the contact part which is located on the side of the connecting part is provided with a cushion.

Subject matter of the invention is also a system for delivering respiratory gas directly into the nose of a user, comprising:
 a set according to the invention, and
 a supply tube,
 the supply tube penetrating the bore of the connecting part of the retaining device and entering into at least one portion of the passage of the inserted part of the device of the set.

According to another embodiment, the supply tube has a lateral hole, the cushion of the contact part of the retaining device is inflatable, and the connecting part has a channel extending from the bore of the connecting part to the contact part, the lateral hole of the supply tube being turned toward the channel in order to conduct the respiratory gas from the tube to the inflatable cushion.

Means for reducing the access of the respiratory gas to the channel are preferably provided on the connecting part.

A further subject matter of the invention is a method for assembling a system according to the invention, wherein a supply tube is led through the bore of the connecting part of a retaining device and is inserted into at least a portion of the passage of the inserted part of the device according to the invention, and if necessary, the spacing apart between said connecting part and the device is adjusted.

BRIEF DESCRIPTION OF DRAWINGS

Embodiments of the invention will be described in the following with reference to the accompanying drawings. Shown are.

DESCRIPTION OF THE EMBODIMENTS OF THE INVENTION

Device According to the Invention

Figure 1:
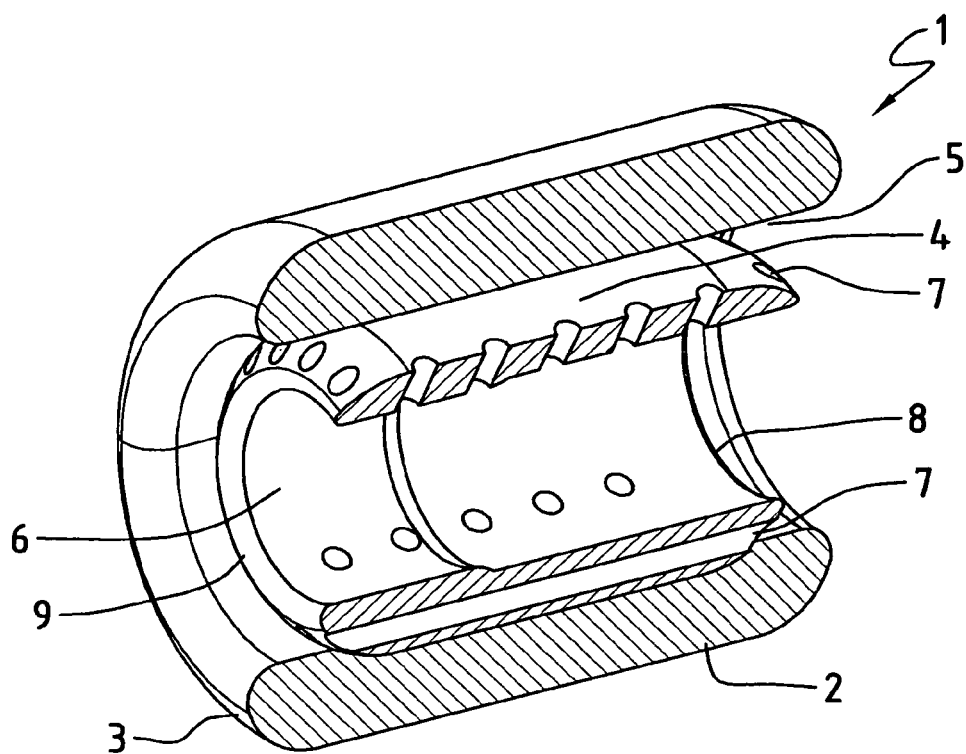
FIG. 1, a perspectival representation of a device according to the invention.

The device 1 according to the invention is shown in FIG. 1. It comprises a hollow membrane 2, which is made of an elastic material. "Elastic" means here that the membrane must be able to adapt to the shape of the nostril. The material can be a natural material, such as, for example, caoutchouc, or a synthetic material, such as, for example, an elastomer. It must be suitable for contact with the nose. To this end it must be taken into consideration that the membrane will remain in the nostril of the user all night long or for several hours (generally 2 to 12 hours). Silicon rubber in particular can be used as material.

The outer dimensions of the membrane are selected such that the membrane can be easily inserted in the nostril of the user.

Preferably, at least the end 3 of the membrane that has to be inserted in the nose is rounded off.

The device 1 according to the invention further comprises a part 4, which is inserted into the cavity 5 of the membrane 2. This part 4 has a passage 6. Located in the walling of the inserted part 4 are breathing channels 7, which are preferably distributed evenly around the passage 6. Both the passage 6 and the breathing channels 7 extend from one end 8 to an opposite end 9 of the inserted part 4.

The passage 6 normally makes possible the supply of respiratory gas to the user, and the breathing channels 7 normally serve the purpose of exhalation for the user.

According to another embodiment of the invention, however, the passage 6 can serve the purpose of exhalation for the user, and the breathing channels 7 make possible the supply of respiratory gas to the user.

The inserted part 4 is generally composed of a rigid material that cannot cause any nose irritation. Plastics in particular can be used as such material.

Preferably, at least one end 8 or 9 of the part 4 is beveled or rounded off in order to facilitate its insertion in the cavity 5 of the membrane 2.

The membrane 2 and the inserted part 4 are generally cylindrical since this shape is easy to maintain or respectively produce. The passage 6 and the breathing channels 7 generally run parallel to the common axis of the membrane 2 and of the part 4, i.e. from the axial end 8 to the other axial end 9.

The configuration of the breathing channels 7 in the walling of the part 4 advantageously leads to a distribution of the expired air or respectively of the inspired air.

Preferably the breathing channels 7 are disposed evenly or as evenly as possible in the walling of the part 4. This way a medicament can be distributed homogeneously in the nostril during inspiration (when the channels 7 serve as inspiration channels), for example. During expiration, i.e. when the channels 7 are expiration channels, a tingling in the nose of the user is thereby prevented. The inventors have actually noted that a concentration of the expired air in a single, relatively large aperture causes a local cooling in those nose portions through which no expiratory air current flows.

The axial length of the inserted part 4 is generally smaller than the axial length of the membrane 2.

The membrane 2 can have, for example, a diameter of 5 to 8 mm and an axial length of 10 to 15 mm, while the part 4 can have a diameter of 3 to 6 mm and an axial length of 8 to 13 mm. The diameter of the breathing channels 7 amounts to 1 mm, for example.

The cross section of the membrane 2 and of the inserted part 4 could also be oval.

Preferably the inserted part 4 has more than four breathing channels 7, in particular eight.

Figure 2:
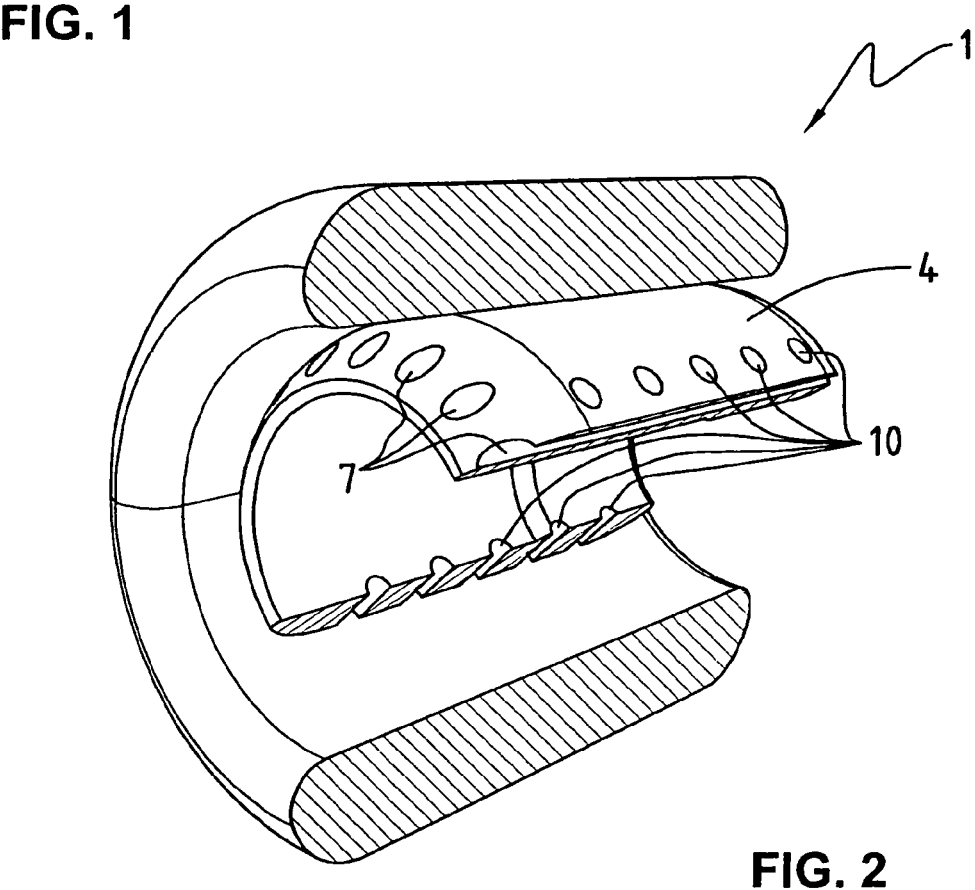
FIG. 2, a view of another embodiment of the device according to the invention.

According to one embodiment, which is shown in FIG. 2, the inserted part 4 has at least one transverse hole 10 extending in the walling of the inserted part 4 between the passage 6 and the outer surface. This transverse hole 10 serves to generate a pressure against the membrane 2, which advantageously leads to a positioning and fixing of the device 1 in the nostril of the user. The diameter of this transverse hole 10 amounts to 1 mm, for example.

Preferably a multiplicity of transverse holes 10 is present, for instance twelve. The openings of these transverse holes 10 are preferably disposed on the outer surface of the inserted part 4 in such a way that a pressure is exerted on the inner surface of the membrane 2 in all radial directions. Of course the transverse holes 10 are not connected to the breathing channels 7.

Production of the Inventive Device

To produce the device 1, the part 4 is inserted in the membrane 2. The membrane 2 is then attached to the part 4. This attachment can take place chemically (e.g. through vulcanization), thermally (e.g. through laser radiation or ultrasonic welding), or by any other suitable method.

Preferably only the ends of the membrane 2 are attached to the ends of the part 4 in an airtight way. In a device with transverse holes 10, owing to the pressure of the respiratory gas between its attached ends, the membrane 2 moves away from the part 4. The membrane 2 thus adapts itself optimally to the shape of the nostril, and the device is firmly seated in the nose of the user.

Set According to the Invention

The set according to the invention includes a device according to the invention and a retaining device for maintaining the device in a nostril of the user.

This retaining device is preferably configured to be attached to a supply tube that supplies the respiratory gas in the nose.

Figure 3:
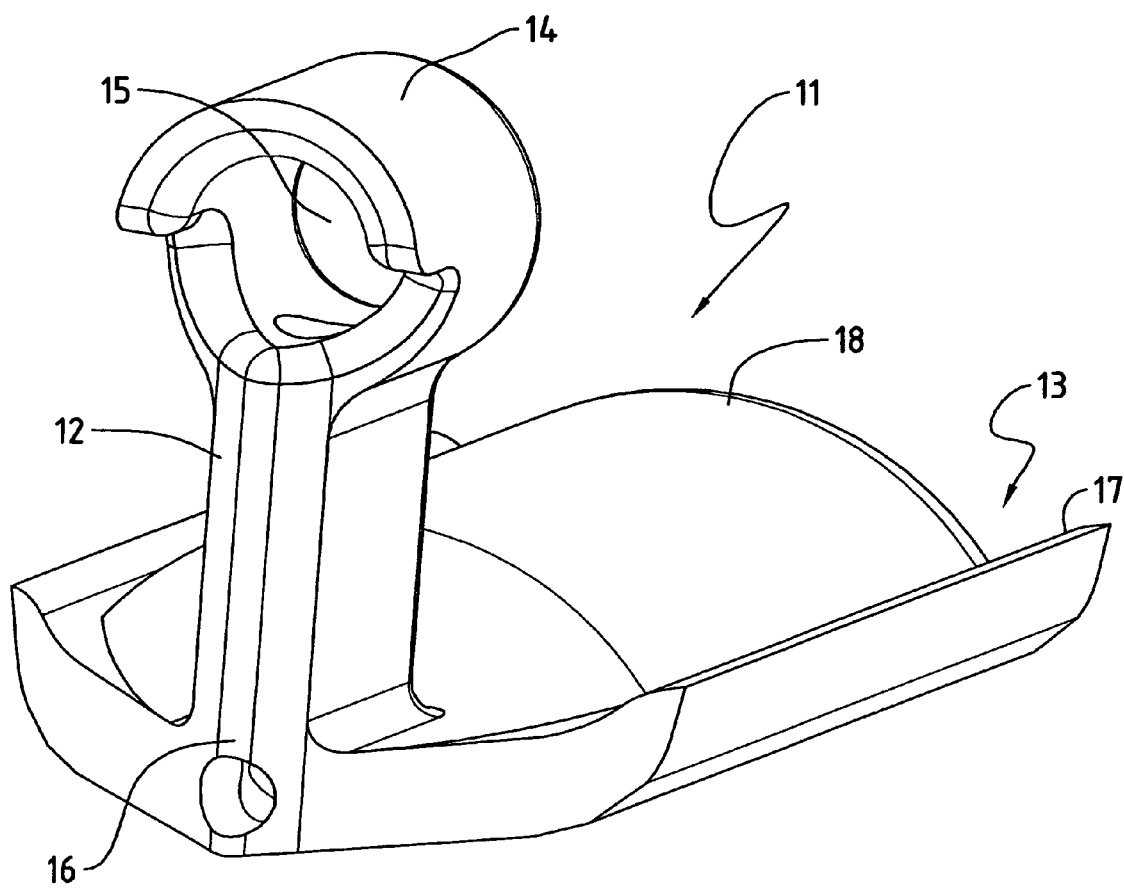
FIG. 3, a perspectival representation of a retaining device for holding the device according to the invention in a nostril of the user.

Such a retaining device 11 is shown in FIG. 3. It has a connecting part 12 and a contact part 13.

The connecting part 12 has a substantially elongated shape. It has at one end 14 a bore 15, which is suitable for mounting the supply tube. The axis of the bore 15 is substantially perpendicular to the longitudinal axis of the connecting part 12.

Located at an opposite end 16 of the connecting part 12 is the contact part 13. This has substantially the shape of a plate that is turned toward the axis of the bore, i.e. the plane which is formed by the main surfaces of the plate forms a substantially right angle with the longitudinal axis of the connecting part 12.

The retaining device 11, in particular the connecting part 13, generally consists of a plastic which is suitable for contact with the nose.

Preferably the surface 17 of the contact part located on the side of the bore 15 is provided at least partially with a cushion 18. This cushion 18 can consist of materials such as e.g. polytetrafluoroethylene (PTFE) or expanded PTFE. It can be stiff or soft.

The spacing apart between the contact part 13 or, if applicable, the cushion 18, and the membrane 2 normally corresponds to the thickness of an alar wing of the nose, i.e. 2 to 3 mm.

System According to the Invention and its Assembly

Figure 4:
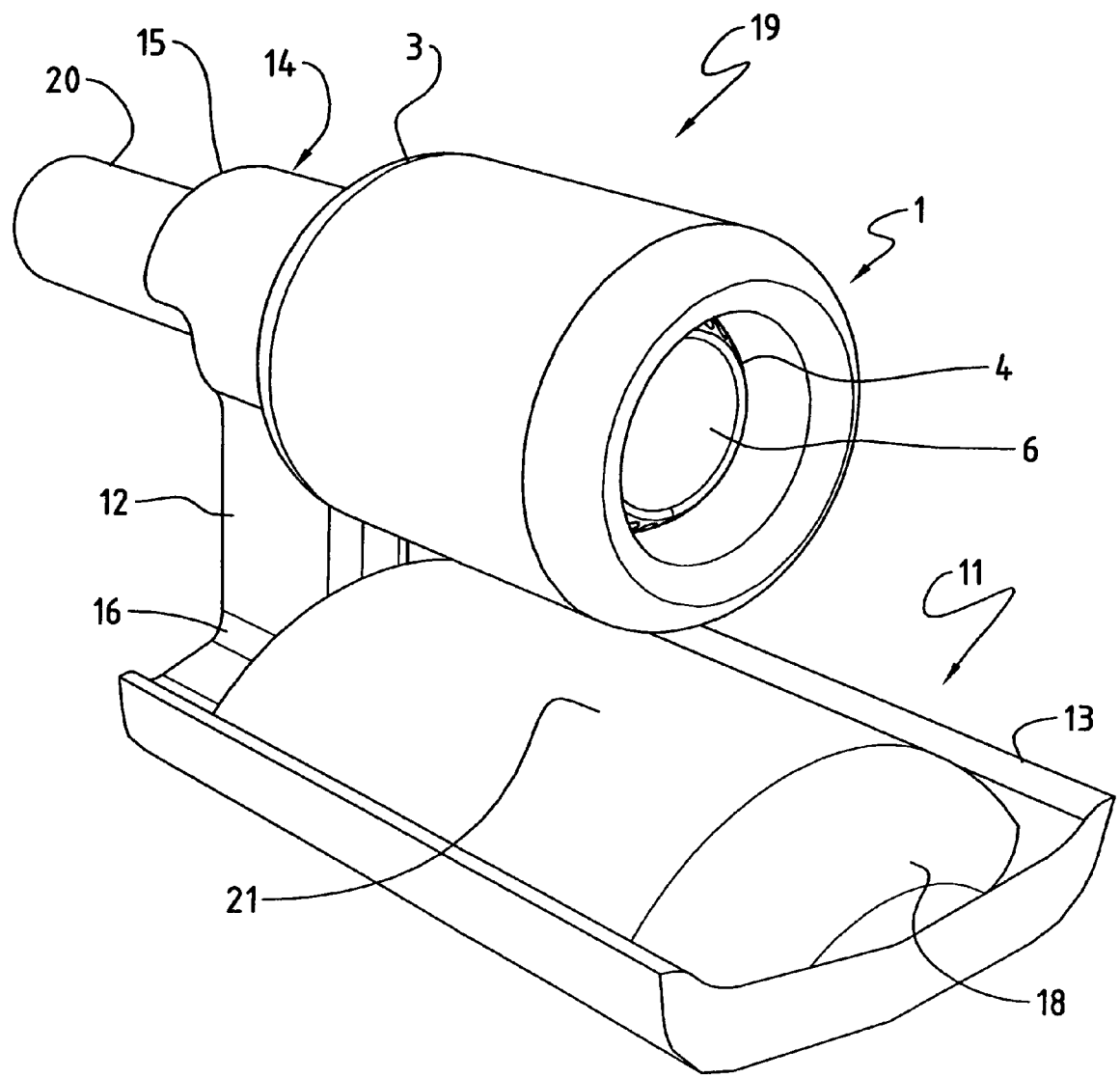
FIG. 4, a perspectival representation of a system according to the invention.

The system according to the invention 19 is shown in FIG. 4. It comprises a set according to the invention and a supply tube 20 which is intended for supply of respiratory gas in the nose.

The supply tube 20 penetrates the bore 15 of the retaining device 11 and at least into a portion of the passage 6 of the inserted part 4. The axis of the device 1 is thus parallel to the plane formed by the main surfaces of the contact part 13.

An interim space 21 is formed by the device 1 and the contact part 13 and the possible cushion 18.

To assemble this system, first the supply tube 20 can be led through the bore 13, for example, and then inserted into at least one portion of the passage 6 of the inserted part 4 of the device 1. For the case where the part 4 has transverse holes 10, one of course avoids inserting the supply tube 20 into the entire passage 6; otherwise these transverse holes 10 will be blocked.

The diameter of the bore 15 is selected such that a little play results between the bore 15 and the supply tube 20.

The diameter of the passage 6 is selected such that there is no play between the supply tube 20 and the passage 6, so that the supply tube 20 is firmly held in the passage 6.

There can exist an axial spacing apart between the end 14 of the connecting part 12 and the end 3 of the device 1.

Figure 5:
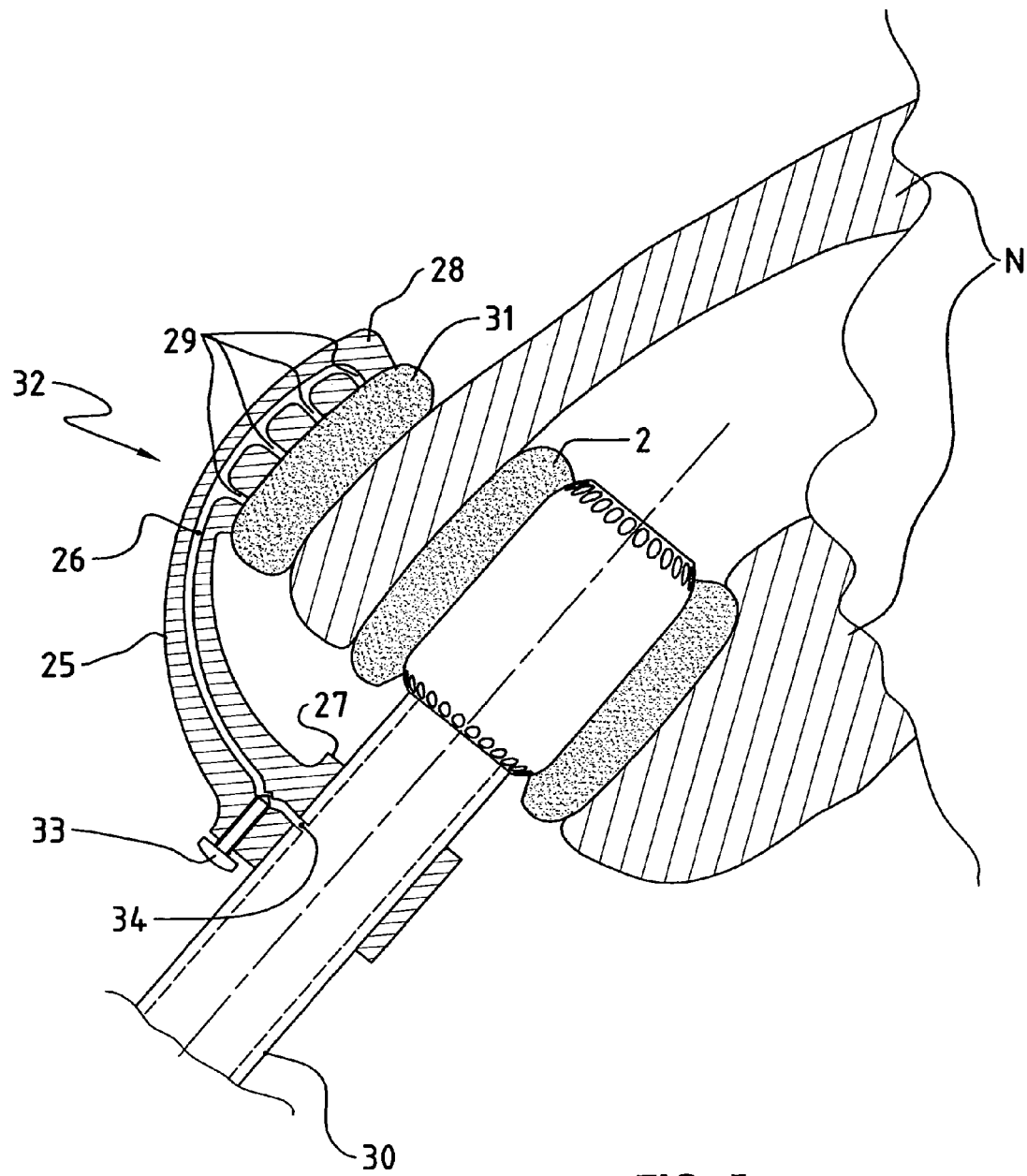
FIG. 5, a perspectival representation of another system according to the invention with a curved connecting part.

Shown in FIG. 5 is another embodiment of the system according to the invention.

The connecting part 25 of the retaining device 32 here has a channel 26 extending from the bore 27 of the connecting part 25 to the contact part 28. On the contact part 28, the channel 26 ends with at least one nozzle 29, which comes out into an inflatable cushion 31.

In addition to its normal opening, the supply tube 30 has a lateral hole 34, which is turned toward the channel 26, in order to conduct the respiratory gas from the supply tube 30 to the inflatable cushion 31.

This way the respiratory gas can flow through the lateral hole 34, the channel 26 and the nozzle 29, and inflate the cushion 31. The alar wing is thereby pressed between the cushion 31 and the membrane 2, and the system according to the invention is fixed to the nose N of the user.

During assembly of the system of FIG. 5, the supply tube 30 is rotated, if necessary, until its lateral hole 34 comes out into the channel 26.

Means 33 are also preferably provided, such as a valve on the connecting part 25 on the side of the bore 27, which means 33 reduce the access of the respiratory gas to the channel 26, in order to adjust or respectively decrease the pressure of the cushion 31 on the alar wing of the user.

Use of the System according to the Invention

A sleep apnea syndrome is diagnosed today solely by a pneumologist who then prescribes the suitable therapy. The individual setting of the CPAP device and the adjustment and monitoring of the system according to the invention can take place in a sleep lab.

The dimensions of the device and retaining device according to the invention as well as the axial spacing between the device and the connecting part of the retaining device are determined or set depending upon the user or patient.

The device according to the invention and, if applicable, the associated retaining device are preferably intended for one-time use, and are disposed of after being used.

Figure 6:
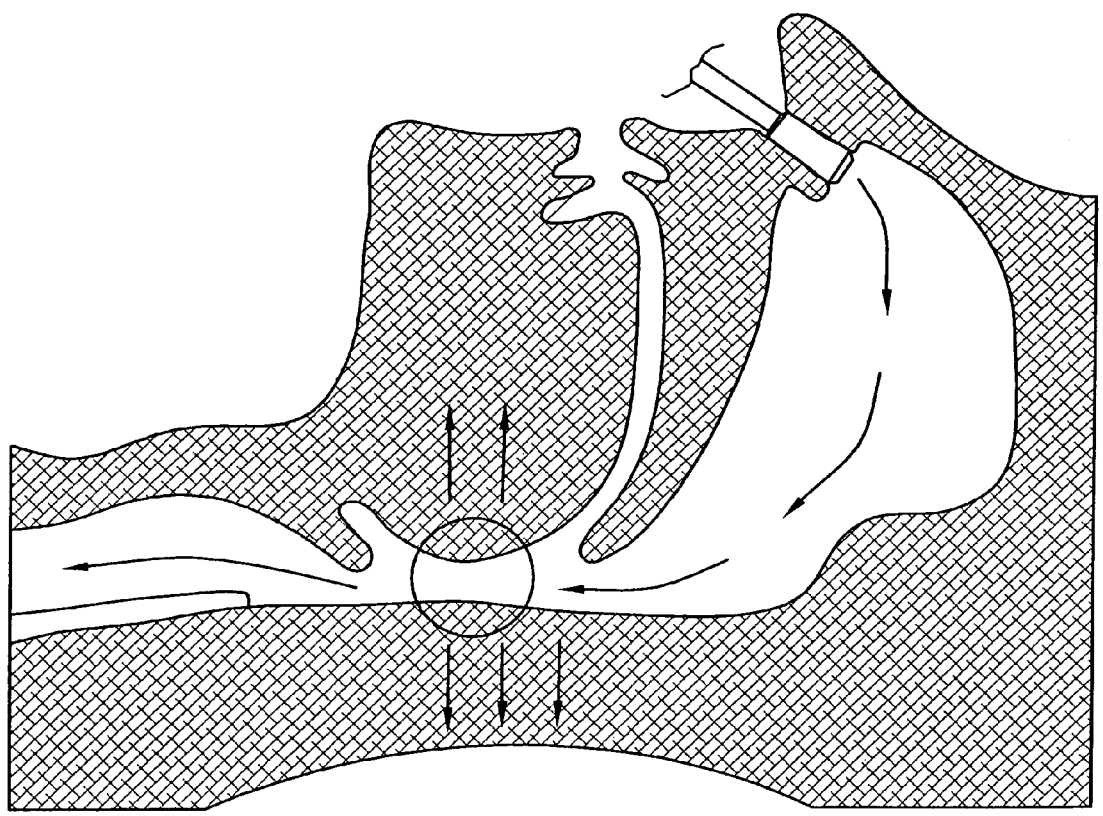
FIG. 6, a portion of the head of a user during use of the system according to the invention.

Shown in FIG. 6 is an example of use. The user or patient inserts the device according to the invention in a nostril. The corresponding alar wing is then clamped through the co-operation of the device and the retaining device (not shown), whereby the system is held firmly. This attachment withstands all head and body movements during sleep of the user. Normally two systems according to the invention are used simultaneously. The supply tube 20 or 30 can then be connected to the compressed air hose of a ventilator (or of a pump). If necessary, the user adjusts the flow of the respiratory gas or respectively the pressure on his alar wing by acting upon the means 33 (see FIG. 5).

It can happen that the user does not need any retaining devices, and uses the devices by themselves.

With the system according to the invention, the respiratory air generated by a CPAP device with slightly elevated overpressure is supplied directly into the nose of the user or patient. A treatment of sleep apnea without uncomfortable face masks and bothersome headbands thereby becomes possible for the first time.

This way the restrictions for the user or patient are considerably reduced, the use of the supported respiration is simplified, and the acceptance of the therapy significantly improved.

The invention claimed is:
1. A device for delivering respiratory gas directly into a nose of a user, comprising:
a hollow elastic membrane that is insertable into a nostril of the user; and a part, inserted in the cavity of the elastic membrane, wherein the part has a passage extending longitudinally from one end to an opposite end of the part, and wherein the part further comprises breathing channels located within and enclosed by a walling of the part, and the breathing channels extend longitudinally from one end to an opposite end of the part and each have respective openings at the one end and the opposite end, and wherein the breathing channels are fluidly connected with ambient air at the one end of each breathing channel during use, and the opposite end of each breathing channel is positioned relatively farther up the user's nostril during use as compared to the one end of each breathing channel.

2. The device according to claim 1, wherein the part has at least one transverse hole, in the walling of the part, which extends between the passage and the outer surface of the part.

3. The device according to claim 1, wherein the membrane has at least one rounded off end.

4. The device according to claim 1, wherein the part has at least one rounded-off or beveled end.

5. The device according to claim 1, wherein the membrane and the part are substantially cylindrical.

6. The device according to claim 1, wherein the membrane is made of rubber.

7. The device according to claim 1, wherein the part is made of plastic.

8. A method for producing the device of claim 1, comprising:
   inserting the part into the cavity of the hollow elastic membrane insertable into the nostril of the user; and
   fixing the membrane to the part.

9. A set for delivery of respiratory gas directly into a nose of a user, comprising:
   a device for delivering respiratory gas directly into the nose of a user that includes a hollow elastic membrane adapted to be insertable into a nostril of the user;
   a part inserted in the cavity of the elastic membrane,
      wherein the part has a passage extending longitudinally from one end to an opposite end of the part;
      wherein the part further comprises breathing channels which are located within and enclosed by a walling of the part and the breathing channels extend longitudinally from one end to an opposite end of the part and each have respective openings at the one end and at the opposite end, and the breathing channels are fluidly connected with ambient air at the one end of each breathing channel during use, and the opposite end of each breathing channel is positioned relatively farther up the user's nostril during use as compared to the one end of each breathing channel, or a device produced through the method according to claim 8; and
   a retaining device for holding said device in the nostril of the user.

10. The set according to claim 9, wherein the retaining device is attachable to a supply tube adapted to dispense the respiratory gas.

11. The set according to claim 10, wherein the retaining device has a connecting part and a contact part.

12. The set according to claim 11, wherein the connecting part has a bore at one end for the supply tube and in that the contact part is located at an opposite end of the connecting part.

13. The set according to claim 12, wherein the contact part has substantially the form of a plate that is turned toward the axis of the bore.

14. The set according to claim 13, wherein a surface of the contact part that is located on the side of the connecting part is provided with a cushion.

15. The set according to claim 9, wherein the retaining device is made of plastic.

16. A system for delivering respiratory gas directly into a nose of a user, comprising:
   a set according to claim 9; and
   a supply tube,
      wherein the supply tube is adapted to penetrate a bore of a connecting part of the retaining device and entering into at least one portion of the passage of the part of the device of said set.

17. The system according to claim 16, wherein the supply tube has a lateral hole, a cushion of a contact part of the retaining device is inflatable, and the connecting part has a channel extending from the bore of the connecting part to the contact part, the lateral hole of the supply tube being turned toward the channel.

18. The system according to claim 17, wherein provided on the connecting part are means for reducing access for the respiratory gas to the channel.

19. A method for assembling a system according to claim 16, comprising:
   leading the supply tube through the bore of the connecting part of the retaining device;
   inserting the supply tube into the passage of the part; and
   if necessary, adjusting the spacing between said connecting part and said device.

20. The method according to claim 19, wherein the supply tube is rotated until a lateral hole comes out into a channel of the connecting part.

* * * * *